United States Patent
Marchesini

(10) Patent No.: US 11,432,576 B2
(45) Date of Patent: *Sep. 6, 2022

(54) HEAT STERILIZED HIGH PROTEIN ENTERAL COMPOSITIONS WITH WHEY PROTEIN WHICH COMPRISES WHEY PROTEIN MICELLES AND A SOURCE OF CASEIN

(71) Applicant: NESTEC S.A., Vevey (CH)

(72) Inventor: Giulia Marchesini, Bern (CH)

(73) Assignee: Societe des Produits Nestle S.A., Vevey (CH)

( * ) Notice: Subject to any disclaimer, the term of this patent is extended or adjusted under 35 U.S.C. 154(b) by 78 days.

This patent is subject to a terminal disclaimer.

(21) Appl. No.: 16/308,507

(22) PCT Filed: Jun. 7, 2017

(86) PCT No.: PCT/EP2017/063762
§ 371 (c)(1),
(2) Date: Dec. 10, 2018

(87) PCT Pub. No.: WO2017/211856
PCT Pub. Date: Dec. 14, 2017

(65) Prior Publication Data
US 2019/0159503 A1     May 30, 2019

(30) Foreign Application Priority Data
Jun. 10, 2016 (EP) ..................... 16174067

(51) Int. Cl.
*A23L 33/19* (2016.01)
*A23L 2/39* (2006.01)
*A23L 2/66* (2006.01)
*A23L 33/00* (2016.01)
*A23J 3/10* (2006.01)
*A23J 3/14* (2006.01)

(52) U.S. Cl.
CPC ................. *A23L 33/19* (2016.08); *A23J 3/10* (2013.01); *A23L 2/39* (2013.01); *A23L 2/66* (2013.01); *A23L 33/30* (2016.08); *A23L 33/40* (2016.08); *A23J 3/14* (2013.01); *A23V 2002/00* (2013.01); *A23V 2200/33* (2013.01); *A23V 2250/5488* (2013.01); *A23V 2250/54246* (2013.01); *A23V 2250/54252* (2013.01); *A23V 2300/24* (2013.01); *A23V 2300/26* (2013.01)

(58) Field of Classification Search
CPC .......... A23L 33/19; A23L 33/30; A23L 33/40; A23L 2/39; A23L 2/66; A23J 3/10; A23J 3/14; A23V 2002/00; A23V 2300/26; A23V 2200/33; A23V 2250/54246; A23V 2250/54252; A23V 2250/5488; A23V 2300/24
USPC ........ 426/580, 583, 656, 657, 520, 521, 522
See application file for complete search history.

(56) References Cited

U.S. PATENT DOCUMENTS

| 5,882,705 | A  | 3/1999  | Sato et al. |
|-----------|----|---------|-------------|
| 8,846,759 | B2 | 9/2014  | Luiking et al. |
| 8,853,148 | B2 | 10/2014 | Miller et al. |
| 2009/0304866 | A1 | 12/2009 | Bovetto et al. |
| 2011/0046048 | A1 | 2/2011  | Minor et al. |
| 2013/0210715 | A1 | 8/2013  | Greenberg et al. |
| 2014/0249078 | A1 | 9/2014  | Breuille et al. |

(Continued)

FOREIGN PATENT DOCUMENTS

| EP | 1839492      | 10/2007 |
|----|--------------|---------|
| JP | H09238614 A  | 9/1937  |
| JP | 2013176357   | 9/2013  |

(Continued)

OTHER PUBLICATIONS

JP 2013176357, Sep. 2013, translation.*

(Continued)

*Primary Examiner* — Leslie A Wong
(74) *Attorney, Agent, or Firm* — K&L Gates LLP

(57) ABSTRACT

The present invention is directed to a liquid heat sterilized enteral composition comprising: a protein source in an amount of 12 to 20% by weight of the composition, the protein source consisting of whey protein containing whey protein micelles and a source of casein. The inventive heat sterilized enteral composition preferably has a cysteine content of 1.2 to 2.4% by weight of the composition. The present invention is furthermore directed to a process for preparing a heat sterilized enteral composition comprising protein in an amount of 12 to 20% by weight based on the weight of the composition, said protein consisting of whey protein containing whey protein micelles and casein, which comprises the steps of: (i) Providing an aqueous solution of a protein source consisting of whey protein containing whey protein micelles and (ii) Adding a protein source containing casein; (iii) Optionally performing a homogenization treatment step; (iv) Performing a heat treatment step; (v) Optionally performing a homogenization treatment step. Finally, the invention concerns the use of a protein source consisting of whey protein containing whey protein micelles and a source of casein, for preparing an enteral composition and/or for controlling the viscosity of a liquid enteral composition, wherein the enteral composition comprises 12 to 20 weight % total protein. The invention also concerns medical uses and treatments applying or using the inventive heat sterilized enteral composition.

19 Claims, 5 Drawing Sheets

(56) References Cited

U.S. PATENT DOCUMENTS

Figure 1:
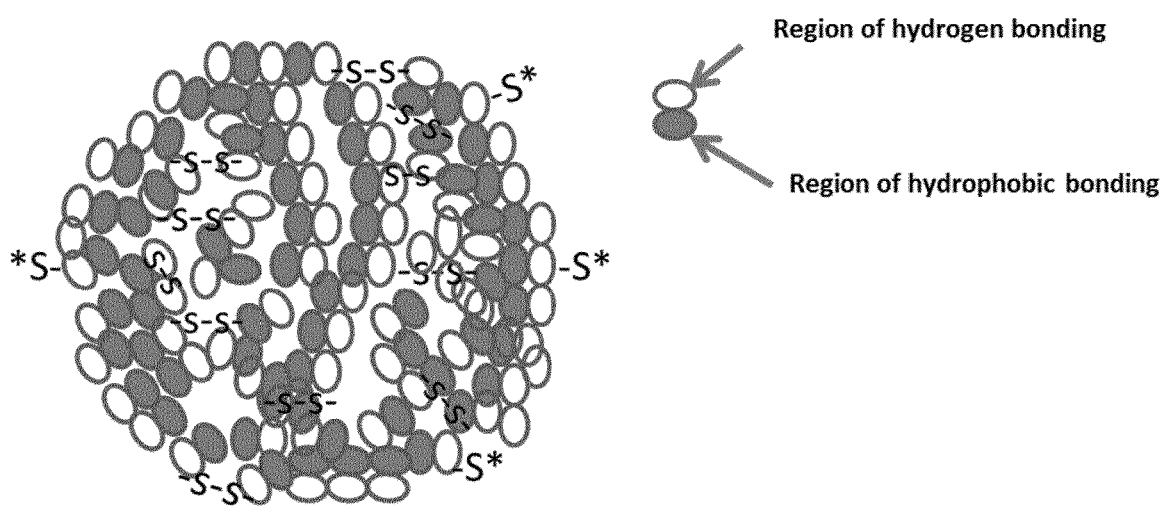

2015/0351437 A1  12/2015  Veneman et al.
2019/0159504 A1   5/2019  Marchesini

FOREIGN PATENT DOCUMENTS

WO    2010043415    4/2010
WO    2012081971    6/2012
WO    2015156662   10/2015

OTHER PUBLICATIONS

Mintel "Massa Mix", Jul. 2013, retrieved from www.gnpd.com, Database accession No. 2111129, 3 pages, XP002765417.
Anonymous "MuscleTech Micellar Whey: Power of Whey at the Speed of Casein" Mar. 11, 2015, retrieved from the Internet at URL:https://blog.priceplow.com/supplement-news/muscletech-micellar-whey, pp. 1-6, XP002765418.
China Patent Office Communication for Application No. 201780030310.X, dated Jan. 6, 2022, 17 pages.

* cited by examiner

HEAT STERILIZED HIGH PROTEIN ENTERAL COMPOSITIONS WITH WHEY PROTEIN WHICH COMPRISES WHEY PROTEIN MICELLES AND A SOURCE OF CASEIN

CROSS REFERENCE TO RELATED APPLICATIONS

The present application is a National Stage of International Application No. PCT/EP2017/063762, filed on Jun. 7, 2017, which claims priority to European Patent Application No. 16174067.5, filed on Jun. 10, 2016, the entire contents of which are being incorporated herein by reference.

FIELD OF THE INVENTION

The present invention is directed to a liquid heat sterilized enteral composition comprising: a protein source in an amount of 12 to 20% by weight of the composition, the protein source consisting of whey protein containing whey protein micelles and a source of casein. The inventive heat sterilized enteral composition preferably has a cysteine content of 1.2 to 2.4% by weight of the composition. The present invention is furthermore directed to a process for preparing a heat sterilized enteral composition comprising protein in an amount of 12 to 20% by weight based on the weight of the composition, said protein consisting of whey protein containing whey protein micelles and casein, which comprises the steps of: (i) Providing an aqueous solution of a protein source consisting of whey protein containing whey protein micelles and (ii) Adding a protein source containing casein; (iii) Optionally performing a homogenization treatment step; (iv) Performing a heat treatment step; (v) Optionally performing a homogenization treatment step. Finally, the invention concerns the use of a protein source consisting of whey protein containing whey protein micelles and a source of casein, for preparing an enteral composition and/or for controlling the viscosity of a liquid enteral composition, wherein the enteral composition comprises 12 to 20 weight % total protein. The invention also concerns medical uses and treatments applying or using the inventive heat sterilized enteral composition.

BACKGROUND

It is often advantageous to provide enteral compositions containing a high protein content. This comes about since for instance an elderly person's ability to consume products may diminish. Alternatively, a sportsman or sportswoman whilst participating in sport may be in need of nutrition whilst the time taken to consume said nutrition should not impede their performance.

However, when increasing calories and/or the concentration of proteins in a nutritional liquid enteral composition this increases the overall product viscosity and decreases the stability (e.g. resulting in gelation or precipitation during process or upon storage), also having a disadvantageous effect on the palatability of the composition. An increased viscosity can make the liquid nutritional composition difficult to consume or administer, and can also diminish the taste of the composition. Furthermore, the stability of such protein and energy dense liquid products may become a problem One method to decrease the viscosity of a nutritional product containing protein is to hy-drolyze the protein source therein, or to employ a hydrolyzed protein source for the preparation thereof. However, such methods although allowing a reduced viscosity generally suffer the disadvantage that as a result of the hydrolysis a product with a bitter taste is provided.

Conventional protein hydrolysis processes are based on batch processes such as simple batch processes—including enzyme inactivation after hydrolysis time by product transfer to a heating unit. On an industrial scale batch processes often require a significant length of time, typically at least 1 to 3 hours. Furthermore, such processes allow little control re-garding the degree of hydrolysis of the protein source and as a result provide products which are substantially bitter in taste. An example of such a batch process is for instance described in WO 2012/042013 A1.

In these processes many factors influence the process of hydrolysis, which makes these processes difficult to control and lead to a high risk that products are obtained have either high bitterness or are inadequate due to being too viscous.

Another method to decrease the viscosity of a nutritional product containing protein is to include micellar casein or cross-linked micellar casein as described in EP 2 230 940 B1 and WO 2015/156672 respectively, although neither exploit whey protein micelles as per the present invention. The requirement of modifying the micellar casein by cross linking means that such products may be viewed as not being "all natural", which may be seen as disadvantageous by the consumer. Also, said methods do not entirely prevent products obtained with micellar casein or cross-linked micellar casein that are bitter in taste.

Finally, whey proteins are an excellent source of essential amino acids (AA) (45%). Compared to casein (containing 0.25 g cysteine/100 g protein), sweet whey proteins contain 7 times more cysteine, and acid whey 10 times more cysteine. Cysteine is the rate limiting amino acid for glutathione (GSH) synthesis, a tripeptide made of glutamate cysteine and glycine which has primary important functions in the defence of the body in case of stress. Requirements in these amino acids may be increased in case of stress and in elderly people.

Also, glutathione oral supplementation with whey protein has been shown to increase plasma GSH levels of HIV-infected patients (Eur. J. Clin. Invest. 2001; 31, 171-178).

Other health benefits provided by whey proteins include enhancement of muscle develop-ment and building, as well as muscle maintenance in children, adults or elderly people, enhancement of the immune function, improvement of cognitive function, control of blood glucose such that they are suitable for diabetics, weight management and satiety, anti-inflammatory effects, wound healing and skin repair, lowering of the blood pressure, etc.

Whey proteins have a better protein efficiency ratio (PER=118) compared for example to casein (PER=100). PER is a measure of a protein quality assessed by determining how well such protein supports weight gain. It can be calculated by the following formula:

PER=body weight growth($g$)/protein weight intake($g$).

| Examples:    | PER | % Casein |
|--------------|-----|----------|
| casein       | 3.2 | 100      |
| Egg          | 3.8 | 118      |
| Whey         | 3.8 | 118      |
| Whole Soya   | 2.5 | 78       |
| Wheat gluten | 0.3 | 9        |

In view of the above, the problem underlying the present invention is therefore to provide enteral compositions having a high protein content which are less bitter in taste or preferably are devoid of bitterness. Furthermore, such enteral compositions should have a low viscosity. In addition, such enteral compositions should be rich in essential amino acids (AA), in particular cysteine. Finally, the present invention is confronted with the problem of providing a process allowing preparing such enteral compositions.

DESCRIPTION OF THE INVENTION

The present inventors have surprisingly found that by employing a protein source consisting of whey protein, and casein, the whey protein preferably containing whey protein micelles, allows low viscosity compositions to be prepared which are not bitter in taste. Furthermore, said compositions may have a high protein content of 8 to 20%, preferably 10 to 20%, more preferably 12 to 20% by weight of the composition whilst at the same time having a low viscosity.

According to the present invention the underlying problem is therefore preferably solved by heat sterilized enteral compositions as described in the independent claims and furthermore a process for preparing such heat sterilized enteral compositions and uses according to independent claims as described herein. The dependent claims advantageously illustrate further preferred aspects of the inventive embodiments.

More preferably, the problem underlying the present invention is solved according to a first embodiment by a heat sterilized enteral composition comprising a protein source in an amount of 12 to 20% by weight of the composition, the protein source consisting of whey protein, the whey protein preferably containing whey protein micelles, and a source of casein.

According to a preferred aspect the heat sterilized enteral composition is a liquid composition. Such a liquid composition preferably has a viscosity of below 200 mPa·s at 20° C. measured at a shear rate of 100 s$^{-1}$, preferably of from 10 to 180 mPa·s at 20° C. measured at a shear rate of 100 s$^{-1}$, preferably 20 to 50 mPa·s at 20° C. or 44 to 120 mPa·s at 20° C. or 50 to 160 mPa·s at 20° C. or 90 to 140 mPa·s at 20° C. or 100 to 150 mPa·s at 20° C. or no to 130 mPa·s at 20° C. or 125 to 160 mPa·s at 20° C., measured at a shear rate of 100 s$^{-1}$. The viscosity may be determined by methods known to a skilled person, e.g. by using a rheometer (Haake Rheostress 6000 coupled with UMTC) equipped with a plate/plate geometry (60 mm diameter) and 1 mm gap. Flow curves with controlled shear rate ramp from 0-300 s$^{-1}$ (linear increase) may be obtained at 20° C.+/−0.1).

According to a preferred aspect the enteral composition of the present invention has total solids in an amount of 25 to 50% by weight of the composition, preferably in an amount of 31 to 44% by weight of the composition.

According to one further preferred aspect the heat sterilized enteral composition may have a caloric density of at least 1.5 kcal/mL of the composition, preferably at least 1.8 kcal/mL, preferably at least 2.0 kcal/mL, preferably at least 2.2 kcal/mL of the composition, preferably wherein the caloric density is typically from 1.5 kcal/mL to 6 kcal/mL or 1.5 kcal/mL to 3.5 kcal/mL 1.8 kcal/mL to 2.4 kcal/mL or 2.3 kcal/mL to 2.8 kcal/mL or from 2.6 kcal/mL to 3.2 kcal/mL.

In some aspects, the inventive heat sterilized enteral composition may have a pH of 5.5 to 8.0, preferably a pH of 6.0 to 7.0, most preferably a pH of 6.0 to 6.5. It is particularly advantageous if the inventive heat sterilized enteral composition has a pH of 6.5 to 7.2, most preferably a pH of 6.7 to 6.9.

Protein Source

According to one aspect of the inventive heat sterilized enteral composition, the protein source as contained therein consists of whey protein, and a source of casein, the whey protein preferably comprising whey protein micelles. In other words, no other proteins are contained in the protein source except of whey protein and a casein source.

Whey Protein

The whey protein as contained in the inventive heat sterilized enteral composition may be selected from e.g. whey protein isolate, acidified whey protein isolate, whey protein concentrate, whey powder, or further whey protein sources. Preferably, the whey protein source is demineralised.

In this light any commercially available whey protein isolates or concentrates may be used, i.e. whey protein obtained by any process for the preparation of whey protein known in the art, as well as whey protein fractions prepared there from or proteins such as [beta]-lactoglobulin (BLG), [alpha]-lactalbumin and serum albumin. In particular, sweet whey obtained as a by-product in cheese manufacture, acid whey obtained as a by-product in acid casein manufacture, native whey obtained by milk microfiltration or rennet whey obtained as a by-product in rennet casein manufacture may be used as the whey protein. The whey protein may be from a single source or from mixtures of any sources. It is preferable that the whey protein does not undergo any denaturation or hydrolysis step prior to micelle formation. Thus, the whey protein typically is not subjected to any enzymatic treatment, heat denaturation or other hydrolysis process prior to the formation of whey protein micelles, i.e. is preferably native whey protein. According to the invention, it is highly preferable that native whey protein be used in the micelle formation process and not hydrolysates thereof.

The present invention is not restricted to whey isolates from bovine origin, but pertains to whey isolates from all mammalian animal species, such as from sheep, goats, horses, and camels.

Also, the inventive heat sterilized enteral composition and also the inventive process according to the present invention applies to mineralised, demineralised or slightly mineralised whey preparations. By "slightly mineralised" is meant any whey preparation after elimination of free minerals which are dialyzable or diafiltrable, but which maintains minerals associated to it by natural mineralisation after preparation of the whey protein concentrate or isolate, for example. These "slightly mineralised" whey preparations have had no specific mineral enrichment.

The whey protein micelles as may be comprised in the whey protein may be obtained from the whey protein by processing and extraction techniques familiar to a person skilled in the art. Such a method for the formation of whey protein micelles may comprise the steps of:

a). Adjusting the pH of a whey protein aqueous solution to a value between pH 3.0 and 8.0, preferably a pH of 5.8 to 7.0, more preferably a pH of 6.0 to 6.5. It is particularly advantageous if the pH of a whey protein aqueous solution is adjusted to a value of between a pH of 6.0 to 6.5, most preferably a pH of 6.2 to 6.4, most preferably a pH of 6.2 to 6.3.

b). Subjecting the aqueous solution to a temperature between 70 and below 95° C. and c). Optionally concentrating the dispersion obtained in step b.

If the whey protein aqueous solution contains a demineralised whey protein, preferably calcium is then added prior to step (b) as described above which forms the micelles.

Most preferably the whey protein micelles as may be employed in the inventive heat sterilized enteral composition have not been subjected to a concentrating step such as optional step c) as shown above.

Preferably, the whey protein micelles as may be contained in the inventive heat sterilized enteral composition are prepared by the inventive process as described herein.

As defined before for the inventive heat sterilized enteral composition, the whey protein containing whey protein micelles has been provided or prepared by techniques familiar to a person skilled in the art. Preferably, the whey protein micelles as may be contained in the inventive heat sterilized enteral composition are prepared by the method for the formation of whey protein micelles as described herein before.

The whey protein micelles as may be obtainable according to a method for the formation of whey protein micelles described herein have not been submitted to any mechanical stress leading to reduction of the particle size during formation. This method induces the formation of whey protein micelles during heat treatment in the absence of shearing.

The whey protein micelles as may be used in the present invention may be produced according to the process described herein but are not limited thereto. The whey protein micelles may also be provided in this context, e.g. as a liquid or in powder form. Such a whey protein micelle preparation may then be added to a whey protein source to provide the whey protein source containing whey protein micelles as defined herein.

Whey protein micelles (WPM) are spherical (regular shape close to natural casein micelles) mono-dispersed micro-gel obtained by auto assembling of native whey proteins during heat treatment at a very specific pH.

WPM have the following unique characteristics and properties:
 A narrow size distribution with a diameter between 100 and 900 nm and a polydispersity index below 0.2
 A turbidity value measured at 500 nm (between 20 and 50 absorbance units for a 4% protein solution) that is stable for 10 minutes
 A spherical shape as imaged by TEM microscopy.

The final architecture of WPM aggregates confers properties like emulsification, micellar casein substitution, whitening, foaming, texturising and/or of filling agents. The WPM are microgels of 20 to 45% whey protein concentration with unique physical characteristics (size, charge, density, size distribution) conferring exceptional behaviours: stable to salt addition, low viscosity at high concentration, gelling between pH 4 and 5 and with high stability against heat treatment used for pasteurization or sterilisation.

WPM are obtained by heat treatment of native whey proteins solution adjusted at a very specific and precise pH at which the net (negative or positive) charge, induced this specific aggregation by auto-assembling. These aggregates are in a particular organised state that results from a balance between repulsive and attractive electrostatic forces associated to hydrophobic interactions and to an asymmetric repartition of charges present at the surface of the proteins.

This phenomena occurs below and above 0.7 pH unit of the iso-electric point (i.e. pH 4.3 and 5.8 for IEP of 5.1) for pure beta-lactoglobulin.

Formation of whey protein micelles does not occur at room temperature because whey protein hydrophobicity is buried into native protein structure.

To induce whey protein micelle formation (formation of spherical mono dispersed protein micro gel by auto-assembling) a protein conformational modification is needed. This modification is induced by heat treatment; during the first early stage of micelle formation. This auto assembling phenomena is reversible by acidification at pH 2.0 just after the optimal temperature was reached (i.e. 85° C.). This very acidic pH block thiol/disulfide interchanges and the non stabilised micelle structure is rapidly dismantled. In normal conditions, without post acidification at pH 2.0, due to thiol activation by the heat treatment, a fast cross linking stabilised the micelle during the incubation at constant temperature (15 min at 85° C.), this incubation time could be prolonged up to 45 min or 120 min. After this incubation, whey protein micelle formation is not spontaneously reversible. Dissociating agent and reducing agent are needed to recover protein units.

Whey protein micelles may be formed by an in situ process in the context of the step (i) of the inventive process, more preferably using the process parameters of step (i) of the inventive process as described above which may also incorporate a method for the formation of whey protein micelles as described before. Alternatively, rather than producing the whey protein micelles in situ, whey protein micelles in the context of the step (i) of the inventive process may be employed by adding the same to the composition of step a) e.g. as a liquid or in the form of a powder.

Preferably, the whey protein micelles preferably contained in the whey protein of the inventive heat sterilized enteral composition, may show a particle size distribution such that more than 80% of the micelles contained therein will have a size smaller than 1 micron. Most preferably, the micelles which may be comprised in the whey protein of the protein source of the inventive heat sterilized enteral composition have a size of between 100 nm and 1200 nm or 400 nm to 900 nm, more preferably between 500 and 770 nm, most preferably between 200 and 350 nm. A whey protein micelle is typically imaged as a spherical shape by Transmission Electron Microscopy (TEM). The mean diameter of the micelles can be measured by Transmission Electron Microscopy (TEM) by methods familiar to a person skilled in the art. Without wishing to be bound by theory, it is thought that during micelle formation, the micelle reach a "maximum" size, due to the overall electrostatic charge of the micelle repelling any additional protein molecule, such that the micelle cannot grow in size any longer. This may account for the narrow size distribution observed.

Furthermore, the whey protein micelles preferably contained in the whey protein of the inventive heat sterilized enteral composition, may be detected in the whey protein contained therein or used therefore or in the final product, i.e. the inventive heat sterilized enteral composition, by various techniques familiar to a person skilled in the art. Preferably following isolation of whey protein micelles, for instance, the ζ-potential thereof may be measured as described in WO 2007/110421, for instance on pages 19 to 20 thereof. In this light, if the ζ-potential measured for the whey protein preferably containing whey protein micelles is more negative than a non-micellised whey protein source ("untreated" whey protein not containing whey protein micelles)—this evidences the presence of whey protein micelles.

Another method which may be used to indicate the presence of whey protein micelles is for instance turbidity measurements, such as by absorbance at 500 nm. An increase in turbidity is associated with whey protein micelle formation as is well known in the art, as described for instance in WO 2007/110421 on page 19, paragraph 2 and FIG. 2 thereof.

Furthermore, the presence of whey protein micelles can also be analyzed for instance by isolating the whey protein micelles contained in the inventive heat sterilized enteral composition, and optionally characterizing the whey protein micelles e.g. by methods as out-lined above. Similarly, the whey protein micelles may be isolated from the protein source as employed in the preparation of the inventive heat sterilized enteral composition or from the final product and optionally characterizing same.

In this light, in the inventive heat sterilized enteral composition as described herein the presence of whey protein micelles may be detected by isolating the whey protein micelles and/or measurement thereof at any step of the preparation of the composition following whey protein micelle formation.

The purity of the whey protein micelles, for instance utilized in the context of the inventive heat sterilized composition, can be obtained by determining the amount of residual soluble whey proteins. Whey protein micelles and casein micelles, if present, are elim-inated by e.g. centrifugation at 20° C. and 26900 g for 15 min. The supernatant is used to determine the whey protein amount by using reversed phase HPLC according to the method of Bordin et al. 2001 (Journal of Chromatography A, 928, 63-76). Values are then usually expressed as a percentage of the initial value before heat treatment. The propor-tion of micelles can be specifically calculated as follows:

$$\text{Proportion of micelles} = \frac{\left(\begin{array}{c}\text{Amount of total proteins} - \\ \text{amount of soluble proteins}\end{array}\right)}{\text{Amount of total proteins}}$$

Casein

Casein as employed in the inventive heat sterilized composition may be selected from any suitable casein source.

Preferably the source of casein in the protein source is selected from at least one of micellar casein, a caseinate salt, milk protein concentrate, milk protein isolate or milk powder; wherein if present the milk powder may be skimmed or full fat. The casein or source of casein may contain micellar casein.

Amount of Protein Source

According to the first defined embodiment the inventive heat sterilized enteral composition contains a protein source in an amount of at least 8% by weight of the composition, preferably a protein source as defined herein.

More preferably, the protein source may be contained in an amount of at least 10% by weight of the composition, at least 12% by weight, at least 14% by weight or at least 16% by weight of the composition. According to a particularly preferred aspect the protein source is present in an amount of 8 to 20% by weight, preferably 11 to 20% by weight or 13 to 20% or 15 to 20% by weight of the composition, alternatively in an amount of from 8 to 15% by weight, or 15 to 20% by weight of the composition.

According to a further preferred aspect the protein source may be present in the inventive heat sterilized enteral composition in a protein concentration of up to 20 g/100 g of the composition, preferably from 11 g/100 g to 20 g/100 g of the composition, preferably from 12 g/100 g to 16 g/100 g, preferably 13 g/100 g to 15 g/100 g of the composition.

Whey Protein Amount

According to a preferred aspect the inventive heat sterilized enteral composition contains whey protein typically in an amount of 4.2 to 14% by weight of the composition, preferably in an amount of 4.5 to 13% by weight of the composition, more preferably in an amount of 4.5 to 10% by weight of the composition, or 4.5 to 9.5% or 4.5 to 9.0% or 4.5 to 8.5% by weight, most preferably between 5.0 and 7.5% by weight of the composition. As noted before, no further proteins in addition to whey protein and casein are present in the protein source employed herein and in the final heat sterilized enteral composition.

Most preferably in the inventive heat sterilized enteral composition the protein source comprising whey protein contains whey protein micelles in an amount based on the whey protein of at least 35%, preferably at least 40% or even 45% or so %; most preferably the protein source comprising whey protein contains whey protein micelles in an amount based on the whey protein of 40 to 60%, more preferably at least 80% based on the whey protein and the residual soluble aggregates or soluble protein content is preferably below 20% based on the whey protein. The average micelle size is characterised by a polydispersity index below 0.260, preferably below 0.200.

Preferably, the inventive heat sterilized enteral composition contains whey protein micelles in an amount of 1.0 to 5% by weight of the composition, most preferably the inventive heat sterilized enteral composition contains whey protein micelles in an amount 2.0 to 3% by weight of the composition, most preferably 2.5 to 3.5% by weight.

Casein Amount

According to a preferred aspect, the inventive heat sterilized enteral composition comprises casein, preferably in an amount of 3.5 to 13% by weight of the composition, most preferably in an amount of 5 to 11% by weight of the composition, preferably 8 to 9% or 8.5 to 10% or 9.5 to 10.5% by weight or any combination of such upper and lower ranges. As noted before, no further proteins in addition to casein and whey protein are present in the protein source employed herein and in the final heat sterilized enteral composition. Most preferably the heat sterilized enteral composition and/or the protein source employed herein comprises whey protein:casein in a weight ratio of 35:65 to 65:35, preferably 40:60 to 60:40, preferably 45:55 to 55:45. In a particularly preferred aspect, casein is present in a whey protein:casein weight ratio of 50:50.

Cysteine

It is particularly advantageous that the heat sterilized enteral composition provides a rich source of cysteine. In this context, preferably the protein source contains whey protein and casein as defined herein. The protein source may not comprise "other proteins" whey protein and casein.

Cysteine Amount

Accordingly, preferably the heat sterilized enteral composition comprises cysteine in an amount of at least 1.2% by weight of the protein source. Preferably the heat sterilized enteral composition comprises cysteine in an amount of 1.2 to 2.4% by weight of the protein source, more preferably a range of between 1.2 to 1.32 and 1.8 to 2.2 by weight of the protein source, such ranges explicitly including amounts of 1.2 to 1.32 and 1.9 to 2.2, e.g. an amount of 1.2 to 2.2% by weight or 1.2 to 2.4% by weight or 1.3 to 2.4% by weight or 1.5 to 2.4% by weight or 1.8 to 2.4% by weight of the protein source.

As defined before, the cysteine content is preferably defined in view of the entire protein content of the protein source. Hereto it is noted that a skilled person, when preparing the composition or when analysing the final heat sterilized enteral composition, can easily distinguish the different ingredients, particularly the amount of milk proteins such as casein and whey protein firstly by separate addition and thus identify the amount of cysteine stemming solely from whey protein and/or casein or both as defined herein.

Since the protein source as used herein is exclusively selected from milk proteins, particularly form whey and casein, the amount of whey protein in relation to the amount of casein can also be determined easily by the quantification of cysteine as described by Nicolai Z. Ballin et. al. in J. Agric. Food Chem. 20016, 54, pages 4131 to 4135 which is incorporated herein by reference.

In this light, Ballin describes that the content of whey protein in casein co precipitate and milk powder was calculated using the formula:

$$\% \text{ whey protein} = (X-0.25)/(3.0-0.25) \times 100$$

Such a calculation preferably allows the amount of cysteine in the heat sterilized enteral composition of the present invention to be calculated, since only milk proteins, such as whey and casein are present.

The quantification of cysteine is an advantageous parameter to measure for the purpose of determining whey protein since the content of cysteine in casein and whey protein differs by more than a factor of 10 and the fact that the cysteine content is independent of protein structure as long as it does not contain cysteine modifications.

Another possibility of measuring the cysteine content follows the European Union (EU) legislation (ECC 2921/90 of 10 Oct. 1990; Off. J. Eur. Commun. 1990, 22-27), which defines the "milk protein content other than casein" (in practice whey protein) to be determined by measuring the —SH and the —S—S— groups linked with proteins.

In this context, milk protein content other than casein' means the content determined by measuring the —SH and —S—S— groups linked with proteins, the reference values being 0.25% and 3% respectively for pure casein and whey protein (ECC 2921/90 of 10 Oct. 1990). Similarly, as above, the cysteine content is preferably determined either in view of the entire protein content of the protein source, since only cysteine and whey protein are contained.

Other Components

Following a further aspect the inventive heat sterilized enteral composition also comprises micronutrients selected from vitamins, minerals, salts and trace elements, which may be present either alone or in combination, preferably in addition to those micronutrients possibly already provided by the protein source.

Alternatively, in some aspects the inventive heat sterilized enteral compositions may also not contain any micronutrients.

The term "micronutrient" as used herein refers to vitamins, (dietary) minerals and/or salts that are required in the human diet in very small amounts. Such micronutrients typically do not comprise proteins.

The term "vitamin" as used herein, refers to any of various organic substances essential in minute quantities to the nutrition of most animals that act especially as coenzymes and precursors of coenzymes in the regulation of metabolic processes. Vitamins have diverse biochemical functions, including function as hormones (for example, vitamin D), antioxi-dants (for example, vitamin C and vitamin E), and mediators of cell signalling, regulation of cell growth, tissue growth and differentiation (for example, vitamin A). The B complex vitamins, which is the largest in number, function as precursors for enzyme cofactor biomolecules (co-enzymes) that help act as catalysts and substrates in metabolism. For instance Vitamin B6 and Vitamin B12. Other Vitamins, which may be present, include Vitamin K, Thiamin, Riboflavin, Niacin, Folic Acid, Biotin and Pantothenic Acid.

Minerals in this context are preferably dietary minerals such as e.g. calcium, magnesium, phosphorus, potassium, sodium, chloride and sulphur, as well as salts thereof. Preferably, calcium is contained in the inventive heat sterilized enteral composition as a mineral and optionally at least one further dietary mineral as described before.

Further minerals that may be needed and employed in the inventive heat sterilized enteral composition may be trace elements. Such trace elements are typically minerals that are needed in relatively small quantities, for example, chromium, cobalt, copper, chloride, fluorine, iodine, manganese, molybdenum, selenium, and zinc.

Accordingly, in some aspects, the inventive heat sterilized enteral composition can include any combination of vitamins, minerals and trace elements that is useful in providing appropriate nutrition to the patient. The vitamins, minerals and trace elements may be used in the form of a mixture or formulation. The amounts of specific vitamins and minerals in the inventive heat sterilized enteral composition may be determined by one of skill in the art.

The inventors have surprisingly found that low amounts of monovalent metal ions in the inventive heat sterilized enteral composition may further enhance the low viscosity and stability of said composition as defined herein.

According to a preferred aspect the inventive heat sterilized enteral composition comprises a total amount of monovalent metal ions selected typically from Na, K, more the sum of sodium and potassium (Na+K) in a low amount, preferably of up to 40 mg/g of the protein source, preferably less than 25 mg/g of the protein source, most preferably 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source.

In some aspects the amount of potassium in the inventive heat sterilized enteral composition is typically up to 40 mg/g of the protein source, preferably less than 25 mg/g of the protein source, most preferably 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source.

In a further aspect, the amount of sodium in the inventive heat sterilized enteral composition is typically up to 40 mg/g of the protein source, preferably less than 25 mg/g of the protein source, most preferably 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source.

The concentrations of monovalent metal ions in the above paragraphs are based on the total amount of protein in the protein source in the inventive enteral composition, preferably on the total amount of casein, on the total amount of whey protein micelles or on the total amount of whey protein, more preferably based on the total amount of whey protein which comprises whey protein micelles the source of casein as present in the inventive heat sterilized enteral composition.

According to one aspect one or more citrates may also be contained in the inventive enteral composition. Preferably the citrate is tripotassium citrate. Most preferably, the inventive enteral composition comprises citrates in 0.1 to 1% by weight of the composition or 0.3 to 0.7% by weight of the heat sterilized enteral composition. Most advantageously the inventive enteral composition comprises citrates in 0.2 to 0.5% by weight of the composition.

According to a further aspect, the inventive heat sterilized enteral composition also may be provided as a food matrix. A food matrix is defined herein as being any type of food in liquid or powder form, e.g. a beverage, a food supplement, etc. Said food matrix may contain the inventive heat sterilized enteral composition as defined herein and optionally additionally fat and/or carbohydrate.

Preferably, the inventive heat sterilized enteral composition is liquid, and is more preferably provided as a beverage.

According to a particularly preferred aspect, the inventive heat sterilized enteral composition is a nutritional composition, a nutritional supplement, an infant formula, a follow-up formula, a baby food formula, an infant cereal formula or a growing-up milk, an infant or child's food supplement, a children formula, an adult nutritional composition, maternal nutritional supplement, bariatric formula, elderly nutritional composition or health care formula. Furthermore, in some aspects the heat sterilized enteral composition of the present invention may be in form of a supplement or may be used as a sole source of nutrition, e.g. be provided as a full meal. The term "supplement" as used herein refers to a nutrient that may be added to a diet or a meal or beverage thereof.

In the above context, an infant is defined herein as being up to 1 year of age, whereas children are defined as being at least from 1 to 7 years of age.

Furthermore, in this context, follow-up formulae are preferably designed to complement the changing diet of the older infant and provide a more balanced and complete food, better adapted to the child's nutritional needs at this age than normal milk. Growing-up milks (GUMs) can be considered a subgroup of follow-up formulas and are also included into the above-captioned definition. Such GUMs are adapted more particularly to the nutritional needs of children of one year or older, for example 1-6 years. Generally, GUMs are adapted specifically to the nutritional needs of children of a specific age. For example, there are GUMs for children of 1-3 years, 3-5 years and above 5 years old.

Finally, maternal nutrition is typically defined as being for pregnant and lactating women, and furthermore encompasses pre-conception administration to a woman willing to have a baby.

According to one preferred aspect the food matrix optionally may contain in addition to the herein described heat sterilized enteral composition any of a carbohydrate, probiotic, prebiotics, minerals, thickeners, buffers or agents for pH adjustment, chelating agents, colorants, emulsifiers, excipients, flavour agents, osmotic agents, preservatives, stabilizers, sugar, sweeteners, texturizers, and/or vitamins. For example, the nutritional compositions may contain emulsifiers and stabilizers such as soy lecithin, citric acid esters of mono- and di-glycerides, and the like. The optional ingredients can be added in any suitable amount.

According to a specific embodiment, the inventive heat sterilized enteral composition may be used to prepare a food matrix as defined above, preferably a beverage, a food supplement, more preferably a nutritional composition, a nutritional supplement, an infant formula, a follow-up formula, a baby food formula, an infant cereal formula or a growing-up milk, an infant or child's food supplement, a children formula, an adult nutritional composition, maternal nutritional supplement, bariatric formula, elderly nutritional composition or health care formula.

In a further embodiment the inventive liquid heat sterilized enteral composition can also be used as a pharmaceutical and/or a nutraceutical product, preferably as described below.

Yet a further embodiment concerns the use of the inventive heat sterilized enteral compositions as described herein, either as described initially or as obtained or obtainable according to the inventive process as described below, are contemplated. In one embodiment the inventive heat sterilized enteral composition may be used for providing nutrition to a person in need thereof, wherein the person is preferably an elderly person, a person that is in a disease state, a person that is recovering from a disease state, a person that is malnourished, or a healthy person such as a sportsman or sportswoman or an active eh derly.

Within the context of the present invention, the nutritional ingredients of the liquid heat sterilized enteral composition, if provided as a food matrix as defined before, typically include proteins, fats and carbohydrates, which are selected depending on the product type.

Preferably fat is contained in the heat sterilized enteral composition if provided as a food matrix as defined before in 1 to 15% by weight of the composition, preferably 3 to 8% by weight or 5 to 10% or 7 to 12% by weight of the composition.

Preferably carbohydrate is contained in the heat sterilized enteral composition if provided as a food matrix as defined before in 1 to 30% by weight of the composition, preferably 5 to 10% by weight or 8 to 15% or 13 to 20% or 18 to 25% by weight.

Proteins are contained in the heat sterilized enteral composition in an amount as defined above.

A yet further embodiment concerns the use of a protein source consisting of whey protein and a source of casein, the whey protein preferably containing whey protein micelles, as defined herein, for preparing an enteral composition as defined herein comprising 12 to 20 weight % total protein, wherein the composition contains cysteine in an amount of 1.2 to 2.4% by weight of the protein source.

In another embodiment the present invention concerns the use of whey protein, preferably containing whey protein micelles, in combination with a source of casein, preferably as defined herein, for controlling the viscosity of a liquid enteral composition comprising 12 to 20 weight % total protein preferably consisting of whey protein and a source of casein as defined herein, wherein the composition contains cysteine in an amount of 1.2 to 2.4% by weight of the protein source. The composition preferably has a pH of 5.5 to 8, preferably a pH of 6 to 7, preferably a pH of 6.0 to 6.5, most advantageously the composition has a pH of 6.5 to 7.2, most preferably a pH of 6.7 to 6.9.

Preferably, the heat sterilized enteral composition of the present invention could be obtained by any process suitable for a skilled person. More preferably, the heat sterilized enteral composition of the present invention could be obtained by a process as defined in further detailed below.

According to a further embodiment, the object underlying the present invention is therefore preferably also solved by a process for preparing a heat sterilized enteral composition, preferably a heat sterilized enteral composition as defined herein. The present invention hence also describes a heat sterilized enteral composition as described above, preferably a heat sterilized enteral composition obtained or obtainable according to a process for preparing such a composition as defined herein. In this regard, said process may contain or apply any of the amounts and ingredients as defined for the inventive heat sterilized enteral composition.

Process

Hence, according to a particularly preferred embodiment the problem underlying the present invention is solved by a process for preparing a heat sterilized enteral composition comprising a protein source in an amount of 12 to 20% by weight based on the weight of the composition. Said protein source consists of whey protein and a casein source, the whey protein preferably containing whey protein micelles. The process comprises the steps of:
(i) Providing an aqueous solution of a whey protein, preferably containing whey protein micelles;
(ii) Adding a source of casein;
(iii) Optionally performing a homogenization treatment step;
(iv) Performing a heat treatment step as defined herein, preferably above 140° C., and
(v) Optionally performing a homogenization treatment step.

Preferably the steps are carried out in the described order.

Step (i) of the Inventive Process

According to step (i) of the inventive process, an aqueous solution of a protein source is provided consisting of whey protein, preferably containing whey protein micelles.

Preferably the whey protein source or whey protein as provided in the inventive process may be selected from e.g. whey protein isolate, acidified whey protein isolate, whey protein concentrate, whey powder, or further whey protein sources. Preferably the whey protein source is demineralised.

In this light any commercially available whey protein isolates or concentrates may be used, i.e. whey protein obtained by any process for the preparation of whey protein known in the art, as well as whey protein fractions prepared there from or proteins such as [beta]-lactoglobulin (BLG), [alpha]-lactalbumin and serum albumin. In particular, sweet whey obtained as a by-product in cheese manufacture, acid whey obtained as a by-product in acid casein manufacture, native whey obtained by milk microfiltration or rennet whey obtained as a by-product in rennet casein manufacture may be used as the whey protein. The whey protein may be from a single source or from mixtures of any sources. It is preferable that the whey protein does not undergo any hydrolysis step prior to micelle formation. Thus, the whey protein typically is not subjected to any enzymatic treatment or hydrolysis process prior to whey protein micelle formation, i.e. is preferably native whey protein. According to the invention, it is highly preferably that native whey protein be used in the micelle formation process and not hydrolysates thereof.

The present invention is not restricted to whey isolates from bovine origin, but pertains to whey isolates from all mammalian animal species, such as from sheep, goats, horses, and camels. Also, the inventive heat sterilized enteral composition and also the inventive process according to the present invention applies to mineralised, demineralised or slightly mineralised whey preparations. By "slightly mineralised" is meant any whey preparation after elimination of free minerals which are dialyzable or diafiltrable, but which maintains minerals associated to it by natural mineralisation after preparation of the whey protein concentrate or isolate, for example. These "slightly mineralised" whey preparations have had no specific mineral enrichment.

The whey protein micelles as may be contained in the whey protein in step (i) may be provided by processing and extraction techniques familiar to a person skilled in the art.

The whey protein micelles as may be prepared by the inventive process are preferably the whey protein micelles as defined for the inventive heat sterilized enteral composition.

Preferably, the whey protein micelles as may be employed in step (i) of the inventive process are generated by a method for the formation of whey protein micelles comprising the steps of:
a). Adjusting the pH of a whey protein aqueous solution to a value between pH 3.0 and 8.0, most preferably a pH of 5.8 to 7.0, preferably a pH of 6.0 to 6.5. More preferably the pH is adjusted to a pH of 6.0 to 6.4, even more preferably a pH of 6.0 to 6.3;
b). Subjecting the aqueous solution of step a). to a temperature between 70 and below 95° C., preferably between 80 and 85° C. and
c). Optionally concentrating the dispersion obtained in step b.

If the whey protein aqueous solution contains a demineralised whey protein, preferably calcium is then added prior to step b). as described above which forms the micelles.

The method for the formation of whey protein micelles may form an integral substep of step (i).

Most preferably the whey protein micelles as may be employed in for instance steps (i) and (ii) of the inventive process have not been subjected to a concentrating step such as optional step c). of the method for the formation of whey protein micelles as shown above.

Typically in step b). heating at between 70 and below 95° C., preferably between 80 and 85° C. is carried out for e.g. 10 seconds to 2 hours, preferably wherein the heating is carried out for 10 to 20 minutes.

Most preferably following step b). of the method for the formation of whey protein micelles the thus obtained composition comprising preferably micellar whey protein is cooled to a temperature below 20° C., most preferably between 10 to 15° C. At said temperature step (ii) of the inventive process is then preferably carried out.

The whey protein micelles as may be obtained with the method for the formation of whey protein micelles detailed above have most preferably not been submitted to any mechanical stress leading to reduction of the particle size distribution of the generated whey protein micelles during formation. This inventive method preferably induces spontaneous whey protein micelle formation during heat treatment in the absence of shearing.

Most preferably step (i) of the inventive process provides whey protein containing whey protein micelles with a particle size distribution such that more than 80% of the micelles contained therein will have a size smaller than 1 micron. Most preferably, the micelles as may be provided in step (i) of the inventive process have a size of between 100 nm and 1200 nm or 400 nm to 900 nm, more preferably between 500 and 770 nm, most preferably between 200 and 350 nm.

The whey protein micelles may be detected in step (i) and any of steps (ii) to (v) of the inventive method by a number of methods familiar to a person skilled in the art as discussed herein before for the inventive composition. Furthermore, the presence of whey protein micelles may be detected by isolating the whey protein micelles and measurement thereof at any step of the inventive process following whey protein micelle formation preferably using the methods as defined above.

Step (ii) of the Inventive Process

In step (ii) of the inventive process the casein source is added to the aqueous solution of step (i). In this context the casein source as employed in the inventive process may be selected from any suitable casein source.

Preferably, the protein source containing casein may be selected from at least one of micellar casein, native casein, milk protein concentrate, milk protein isolate or milk powder; wherein if present the milk powder may be skimmed or full fat.

In some aspects the protein source provided in step (i) and (ii) of the inventive process or components thereof may be obtained from the corresponding raw materials by processing and extraction techniques familiar to a person skilled in the art, e.g. as described above.

According to one preferred aspect each of steps (i) or (ii) may be followed by a hydration step. This may be advantageous if the whey or casein protein source is added for instance as a powder.

According to the above-defined inventive process the protein sources as employed in the inventive process in steps (i) and/or (ii) are preferably provided in an entire amount of at least 8% by weight of the final heat sterilized enteral composition. More preferably, the protein sources may be provided in an entire amount of at least 10% by weight of the final heat sterilized enteral composition, at least 12% by weight, at least 14% by weight or at least 16% by weight of the final heat sterilized enteral composition, which is obtainable according to the inventive process. According to a particularly preferred aspect, the protein source is provided in an entire amount of 8 to 20% by weight, alternatively in an amount of from 10 to 15% by weight, or 15 to 20% by weight of the final heat sterilized enteral composition.

According to a further preferred aspect the protein source may be provided in the inventive process in a protein concentration of up to 20 g/100 g of the final heat sterilized enteral composition obtainable according to the inventive process, preferably from 11 g/100 g to 20 g/100 g of the final heat sterilized enteral composition obtainable according to the inventive process, preferably from 12 g/100 g to 16 g/100 g, preferably 13 g/100 g to 15 g/100 g of the final heat sterilized enteral composition obtainable according to the inventive process.

Whey Protein Amount

According to a preferred aspect the protein source may be provided in the inventive process such that the final heat sterilized enteral composition contains whey protein, preferably in an amount of 4.5 to 13% by weight of the final heat sterilized enteral composition, most preferably in an amount of 4.5 to 10% by weight of the final heat sterilized enteral composition, or 4.5 to 9.5% or 4.5 to 9% or 4.5 to 8.5%, most preferably 5.0 to 7.5% by weight of the final heat sterilized enteral composition, obtainable according to the inventive process.

According to a particularly preferred aspect the protein source may be provided in step (i) of the inventive process such that the heat sterilized enteral composition obtainable according to the inventive process contains whey protein micelles in an amount based on the amount of whey protein of at least 35%, preferably at least 50 %; most preferably the protein source comprising whey protein contains whey protein micelles in an amount based on the amount of whey protein of 40 to 60%, more preferably at least 80% based on the amount of whey protein. Typically, the residual soluble aggregates or soluble protein content is preferably below 20% based on the amount of whey protein. The average micelle size is characterised by a polydispersity index below 0.260, preferably below 0.200.

In some aspects, the protein source may be provided in step (i) of the inventive process such that the heat sterilized enteral composition obtainable according to the inventive process contains whey protein micelles in an amount of 1.0 to 5% by weight of the composition. Most preferably the inventive process provides a heat sterilized enteral composition containing whey protein micelles in an amount of 2.0 to 3% by weight of the composition, most preferably 2.5 to 3.5% by weight of the composition.

Casein Amount

According to a yet further preferred aspect the casein source may be provided in step (ii) of the inventive process such that the heat sterilized enteral composition contains casein, preferably in an amount of 3.5 to 13% by weight of the composition, most preferably in an amount of 5 to 11% by weight of the composition obtainable according to the inventive process, preferably in an amount of 8 to 9% or 8.5 to 10% or 9.5 to 10.5% by weight, or any combination of such upper and lower ranges. Preferably the "casein source" as defined herein is casein.

Most preferably, the casein source may be provided in step (ii) of the inventive process such that the heat sterilized enteral composition contains casein, preferably in a weight ratio of 35:65 to 65:35, preferably 40:60 to 60:40, preferably 45:55 to 55:45. In a particularly preferred aspect, casein is present in a whey protein/casein weight ratio of 50:50.

Cysteine

It is particularly advantageous that the heat sterilized enteral composition as provided by the inventive process provides a rich source of cysteine. In this context, the protein source solely contains whey protein and casein as defined herein. The protein source may not comprise any other proteins.

Cysteine Amount

To this end, in addition or alternatively, in step (ii) of the inventive process the aqueous solution comprising whey protein, preferably containing whey protein micelles from step (i) and the casein source are mixed such that it contains cysteine preferably in an amount of at least 1.2% by weight of the protein source.

Most preferably, in addition or alternatively, in step (ii) of the inventive process the aqueous solution comprising whey protein, preferably containing whey protein micelles from step (i) and the protein source containing casein are mixed such that it contains cysteine in an amount of 1.2 to 2.4% by weight of the protein source, preferably a range of between 1.2 to 1.32 and 1.8 to 2.2 by weight of the protein source, such ranges explicitly including amounts of 1.2 to 1.32 and 1.9 to 2.2, e.g. preferably in an amount of 1.2 to 2.2% by weight or 1.2 to 2.4% by weight or 1.3 to 2.4% by weight or 1.5 to 2.4% by weight or 1.8 to 2.4% by weight of the protein source.

As defined before, the cysteine content may be preferably defined in view of the entire protein content of the protein source. In this context, in addition to whey protein and casein no "other proteins" are present. Hereto it is noted that a skilled person, when preparing the composition by the inventive process, can easily distinguish the different ingredients, particularly the amount of milk proteins such as casein and whey protein and also of other proteins by separate addition in the steps of the process as described and thus identify the amount of cysteine stemming solely from whey protein and casein as defined herein.

The amount of whey protein in relation to the amount of casein may be determined by the quantification of cysteine as described by Nicolai Z. Ballin et. al. in J. Agric. Food Chem. 20016, 54, pages 4131 to 4135 which is incorporated herein by reference.

In this light, Ballin describes that the content of whey protein in casein co precipitate and milk powder was calculated using the formula:

% whey protein=(X−0.25)/(3.0−0.25)×100

Such a calculation preferably allows the amount of cysteine in the heat sterilized enteral composition of the present invention to be calculated, provided only milk proteins, such as whey and casein are present.

The quantification of cysteine is an advantageous parameter to measure for the purpose of determining whey protein since the content of cysteine in casein and whey protein dif-fers by more than a factor of 10 and the fact that the cysteine content is independent of protein structure as long as it does not contain cysteine modifications.

Another possibility of measuring the cysteine content follows the European Union (EU) legislation (ECC 2921/90 of 10 Oct. 1990; Off. J. Eur. Commun. 1990, 22-27) defining that the "milk protein content other than casein" (in practice whey protein) to be determined by measuring the —SH and the —S—S— groups linked with proteins.

In this context, such milk protein content other than casein', means the content determined by measuring the —SH and —S—S— groups linked with proteins, the reference values being 0.25% and 3% respectively for pure casein and whey protein (ECC 2921/90 of 10 Oct. 1990). Similarly, as above, the cysteine content may be determined either in view of the entire protein content of the protein source, preferably if only cysteine and whey protein are contained but also if other proteins are contained.

Step (iii) and (v) of the Inventive Process

Additionally, according to one other preferred aspect of the inventive process following step (iii) and prior to the homogenization treatment (v) the mixture is preheated to a temperature of 50 to 60° C.

According to one preferred aspect of the inventive process the optional homogenisation step (iii) and (v) are carried out at above 50 bar, preferably at between 50 and 400 bar, preferably between 100 and 400 bar, more preferably between 200 and 350 bar, even more preferably between 250 and 350 bar.

According to a further preferred aspect of the inventive process, following step (iii) preferably the mixture is cooled to below 15° C., preferably at 1 to 5° C. or 3 to 8° C. or 6 to 12° C. Most preferably said cooling is performed prior to performing the optional pH adjustment as defined herein, which may be performed for instance prior to step (iv) of the inventive process. Said optional homogenization may be performed as a two-step homogenisation or a 1 step homogenization. Conditions for the optional homogenization are preferably as defined before, e.g. preferably between 100 and 400 bar, more preferably between 200 and 350 bar, even more preferably between 250 and 350 bar.

Step (iv) of the Inventive Process

According to one preferred aspect of the inventive process the heat treatment step (iv) is performed under UHT conditions, preferably above 140° C., preferably at 141 to 160° C., preferably 141 to 148° C. or 141 to 152° C. or 141 to 155° C., preferably for a time of 1 second to 15 seconds, more preferably for a time of 1 second to 10 seconds, and most preferably for a time of 2.5 seconds to 7.5 seconds, e.g. 3 seconds, 4 seconds, 5 seconds, 6 seconds or 7 seconds, or any value in between or any range formed thereby.

Most preferably, following step (iv) and before optional step (v) of the inventive process the obtained mixture is cooled to below 95° C., preferably below 80° C. or 70° C.; most preferably cooling is performed to 40 to 90° C. or 45 to 55° C. or 50 to 65° C. or 60 to 75° C. or 70 to 85° C. or 80 to 90° C. Most preferably said cooling is flash cooling.

Other Components

In one preferred aspect in step (ii) of the inventive process at least one further component may be added selected from fat, carbohydrate, water or mixtures thereof, which may be added either together or preferably separately. The term fat as used herein may be used interchangeably with the term oil.

Preferably the fat is added in the inventive process such that there is an amount of fat in 1 to 15% by weight of the heat sterilized enteral composition obtainable according to the inventive process, preferably 3 to 8% by weight or 5 to 10% or 7 to 12% by weight of the final enteral composition as obtained after steps (i) to (v).

Preferably the carbohydrate is added in the inventive process such that there is an amount of carbohydrate in 1 to 20% by weight of the heat sterilized enteral composition obtainable according to the inventive process, preferably 3 to 8% by weight or 5 to 10% or 7 to 12% by weight of the final enteral composition as obtained after steps (i) to (v).

Most preferably, the fat is firstly added to the aqueous solution of a protein source comprising whey protein, preferably containing whey protein micelles, as provided in step (i). This may then be followed by the addition of other components such as carbohydrate which may be added separately or together with the protein source containing casein, preferably in step (ii).

Advantageously this may then be mixed by stirring, preferably at a temperature of 5 to 25° C., most preferably at 10 to 15° C. or 12 to 20° C.

Alternatively, following the addition of fat to the aqueous solution comprising whey protein containing whey protein micelles as provided in step (i) of the inventive process rather than mixing using a stirrer the resulting mixture may be homogenized, preferably at 50 to 400 bar, preferably between 100 and 400 bar, more preferably between 200 and 350 bar, even more preferably between 250 and 350 bar. Homogenization is most preferably carried out at 30 to 60° C., preferably 35 to 45° C. or 40 to 55° C. or 50 to 60° C. Said homogenization may be performed as a two-step homogenisation or a 1 step homogenization Additionally, according to one other preferred aspect micronutrients may be added to the protein source, in any of steps (i) to (v) of the inventive process, most preferably following or during step (ii).

Such micronutrients may be selected from vitamins, minerals and trace elements which may be present either alone or in combination. Alternatively, the protein source as employed in the inventive process does not contain any micronutrients or micronutrients may not be added to the inventive process.

According to a particularly preferred aspect a mineral and/or salt content may be added to the protein source, preferably either in step (i) or in step (ii) of the inventive process in an (entire) amount of 1.5 to 5% by weight based on the protein source, preferably 3.5 to 7.5% or even by weight based on the protein source, most preferably 6.25 to 7.25% by weight based on the protein source.

In a further aspect of the inventive process in step (i), preferably also in step (ii), the mineral and/or salt content of the aqueous solution of the protein source is in an amount of less than 2.5% by weight, preferably in an amount of less than 0.2% by weight of the final enteral composition.

The amounts of specific vitamins and minerals to be employed in the inventive process may be determined by one of skill in the art. More preferably, such specific vitamins, minerals and/or their salts are as defined above for the inventive heat sterilised enteral composition.

Further minerals and/or salts that may be added to the protein source, preferably either in step (i) or in step (ii) of the inventive process may be trace elements. Such trace elements may include, for example, chromium, cobalt, copper, chloride, fluorine, iodine, manganese, molybdenum, selenium, and zinc, and/or their salts.

Accordingly, in some aspects, any combination of vitamins can be added in the inventive process, particularly minerals and trace elements that are useful in providing appropriate nutrition to the patient. The vitamins, minerals and trace elements may be added in the form of a mixture or formulation, either as a solution or as a powder or solid.

Furthermore, according to a particularly preferred aspect the heat sterilized enteral compositions obtained following steps (i) to (v) of the inventive process do not have any bitterness.

In some aspects of the inventive process, steps (i) to (ii), preferably also steps (iii) to (v) are carried out at a pH of 5.5 to 8, or a pH of 6 to 7, or a pH of 6.0 to 6.5 or pH; most advantageously steps (iii) to (v) are carried out at a pH of 6.5 to 7.2, most preferably a pH of 6.7 to 6.9. In this light, there may be a pH adjustment performed following or during any of steps (i) to (v), such that the pH is maintained at a pH of 5.5 to 8, preferably a pH of 6 to 7, most preferably a pH of 6.0 to 6.5. Most advantageously during any of steps (i) to (v) the pH is maintained at 6.5 to 7.2, most preferably a pH of 6.7 to 6.9.

According to a preferred aspect of the inventive process generally any acid or base may be used to adjust the pH. Preferably, a base such as KOH is employed to adjust the pH, although other bases including NaOH, sodium carbonate, potassium carbonate, ammonium hydroxide or calcium hydroxide may also be employed to adjust the pH to between pH of 5.5 to 8 or pH of 6 to 7, or a pH of 6.0 to 6.5, most advantageously a pH of 6.5 to 7.2, most preferably a pH of 6.7 to 6.9. Those skilled in the art will recognize other means suitable for adjusting the pH. Suitable acids include, e.g. citric acid, acetic acid and hydrochloric acid.

To this end, in the inventive process only additives are preferably used which do not increase the monovalent metal ion content above 40 mg/g of protein for the reasons as described earlier. For example, the use of potassium citrate or potassium hydroxide for adjusting the pH, or the use of NaCl should preferably be limited or most preferably avoided.

The inventors have surprisingly found that low amounts of monovalent metal ions in the inventive process are particularly advantageous, since this further enhances the low viscosity and stability of the heat sterilized enteral composition as obtained there from.

According to a preferred aspect the protein source comprising whey protein and casein, preferably containing whey protein micelles, i.e. the combined protein sources of steps (i) and (ii), may be provided in the inventive process such that the heat sterilized enteral composition obtainable thereby contains a total amount of monovalent metal ions selected typically from Na and K, more sodium and potassium (Na+K) in a low amount, preferably an amount up to 40 mg/g of the protein source, preferably less than 25 mg/g of the protein source, most preferably 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source.

In some aspects the protein source comprising whey protein and casein, preferably also containing whey protein micelles, i.e. the combined protein sources of steps (i) and (ii), may be provided in the inventive process such that the heat sterilized enteral composition contains potassium typically in up to 40 mg/g of the protein source, preferably less than 25 mg/g of the protein source, most preferably 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source.

In a further aspect aspects the protein source comprising whey protein and casein, preferably containing whey protein micelles may be provided in the inventive process such that the heat sterilized enteral composition obtainable thereby contains sodium typically in up to 40 mg/g of the protein source, preferably less than 25 mg/g of the protein source, most preferably 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source.

The concentrations of monovalent metal ions in the above paragraphs are preferably based on the total amount of protein in the protein source of the obtained/prepared heat sterilized enteral composition, preferably on the total amount of casein, on the total amount of whey protein and typically include the total amount of whey protein.

According to a preferred aspect the protein source comprising whey protein and casein, preferably containing whey protein micelles i.e. the combined protein sources of steps (i) and (ii) may be provided in the inventive process such that the heat sterilized enteral composition obtainable thereby contains one or more citrates. Preferably the citrate is tripotassium citrate. Most preferably, the citrates are added in steps (i) and/or (ii) of the inventive process such that the heat sterilized enteral composition obtainable thereby contains citrates in 0.1 to 1% by weight of the composition, preferably 0.2 to 0.5% by weight or 0.3 to 0.7% by weight of the heat sterilized enteral composition.

In a further aspect of the inventive process following steps (i) to (v) a heat sterilized liquid enteral composition is obtained as a product of the inventive process, the heat sterilized liquid enteral composition preferably being defined as herein above, more preferably said liquid composition preferably having a viscosity of below 200 mPa·s at 20° C. measured at a shear rate of 100 s$^{-1}$, preferably of from 10 to 180 mPa·s at 20° C. measured at a shear rate of 100 s$^{-1}$, preferably 20 to 50 mPa·s at 20° C. or 44 to 120 mPa·s at 20° C. or 50 to 160 mPa·s at 20° C. or 90 to 140 mPa·s at 20° C. or 100 to 150 mPa·s at 20° C. or no to 130 mPa·s at 20° C. or 125 to 160 mPa·s at 20° C., measured at a shear rate of 100 s$^{-1}$.

In some aspects of the inventive process following steps (i) to (v) the heat sterilized enteral composition is in an optional step (vi) dried to form a powder, preferably by spray drying, freeze drying, by lyophylisation or fluid bed agglomeration.

According to a particularly preferred aspect of the inventive process following the homogenization treatment step (iii) and prior to the heat treatment step (iv) the mixture may be cooled to between 0 to 5° C. Said cooling is preferably only performed prior to an optional pH adjustment step to a pH of 5.5 to 8 or a pH of 6 to 7, or a pH of 6.0 to 6.5. It is particularly advantageous that the pH adjustment step is to a pH of 6.5 to 7.2, most preferably a pH of 6.7 to 6.9.

According to a preferred aspect the entire heat sterilized enteral composition obtained following steps (i) to (v) of the inventive process is shelf stable. In some aspects of the inventive process the shelf life is at least 9 months, preferably at least 1 year which preferably commences after either the final process step, more preferably final process step (v). Preferably the heat sterilized liquid enteral composition is shelf stable at room temperature.

Furthermore, in some aspects, the entire heat sterilized enteral compositions obtained following steps (i) to (v) of the inventive process is not substantially bitter in taste and the liquid enteral compositions obtained have a relatively low viscosity, low osmolality which are not jellified and/or not flocculated.

In a further aspect the entire enteral composition obtained following steps (i) to (v) of the inventive process have improved stability, preferably an extended shelf life.

According to a further embodiment, uses of the inventive heat sterilized enteral compositions as described herein, either as described initially or as obtained or obtainable according to the inventive process, are contemplated. In one aspect the inventive enteral composition obtainable according to the inventive process is a beverage composition.

According to one embodiment the inventive enteral composition is particularly suitable for the use in providing nutrition to a person that is in a disease state or a person that is recovering from a disease state or a person that is malnourished.

As used herein, the term "a disease" refers to any derangement or abnormality of function; a morbid physical or mental state.

In some aspects treatment of such diseases or malnourishment is preferably accomplished by administering a therapeutically effective amount of an heat sterilized enteral composition as defined according to the present invention to a subject in need thereof. According to a particularly preferred aspect such a heat sterilized enteral composition is to be admin-istered once daily, preferably twice daily, more preferably three times daily, wherein during administration preferably at least one unit or dose for administration is provided, as defined herein. Upon administration, preferably the total amount of energy to be adminis-tered per day is as defined before. As used herein, the term "subject" refers to an animal.

Preferably, the animal is a mammal. A subject also refers to for example, primates (e.g., humans), cows, sheep, goats, horses, dogs, cats, rabbits, rats, mice, fish, birds and the like. In some aspects preferably the subject is a human.

The term "therapeutically effective amount" of a heat sterilized enteral composition of the present invention refers to an amount of the compound of the present invention that will elicit the biological or medical response of a subject, or ameliorate symptoms, slow or delay disease progression, or prevent a disease, etc. In a further aspect such a "therapeutically effective amount" is a packaged dose or unit as obtained.

According to one embodiment the inventive heat sterilized enteral compositions as described herein, either as described initially or as obtained or obtainable according to the inventive process, are preferably suitable for use in infants (children under the age of 1). In some aspects the inventive enteral compositions are also suitable for use by adults and children.

According to one aspect the heat sterilized enteral composition as described herein, either as described initially or as obtained or obtainable according to the inventive process is a nutritional composition, a nutritional supplement, an infant formula, follow-on formula, a baby food formula, an infant cereal formula or a growing-up milk, infant or child's food supplement, a children formula adult nutritional composition, maternal nutritional supplement, bariatric formula, elderly nutritional composition or health care formula.

In some aspects the heat sterilized enteral composition as described herein, either as described initially or as obtained or obtainable according to the inventive process may be used for providing nutrition to a person in need thereof, wherein the person is preferably an elderly person, a person that is in a disease state, a person that is recovering from a disease state, a person that is malnourished, or a healthy person such as a sportsman or sportswoman or an active elderly.

Various embodiments of the invention have been described above. The descriptions are intended to be illustrative, not limitative. Thus, it will be apparent to one skilled in the art that certain modifications may be made to the invention as described without departing from the scope of the claims set out below.

For example, as described herein, "preferred embodiment" means "preferred embodiment of the present invention". Likewise, as described herein, "various embodiments" and "another embodiment" means "various embodiments of the present invention" and "another embodiment of the present invention", respectively.

Unless otherwise indicated, the term "at least" in the context of the present invention typically preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims, which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having". When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

Furthermore, percentages as described in the present invention can be interchangeably either % weight-by-weight (w/w) or % weight-by-volume (w/v), if not specifically indicated otherwise.

Finally, all publications and patents cited in this disclosure are incorporated by reference in their entirety. To the extent the material incorporated by reference contradicts or is in-consistent with this specification, the specification will supersede any such material.

FIGURES

The following Figures are intended to illustrate the invention further. It is not intended to limit the subject matter of the invention thereto.

FIG. 1: Shows a schematic structure for a whey protein micelle according to the present invention. The whey proteins are arranged in such a way that there are regions of hydrogen bonding and regions of hydrophobic bonding.

Both physical and chemical interactions are involved in the whey protein micelle:

s*: accessible thiol/activated thiol from cysteine.

—S—S—: disulphide bridges stabilizing the whey protein micelle.

Figure 2:
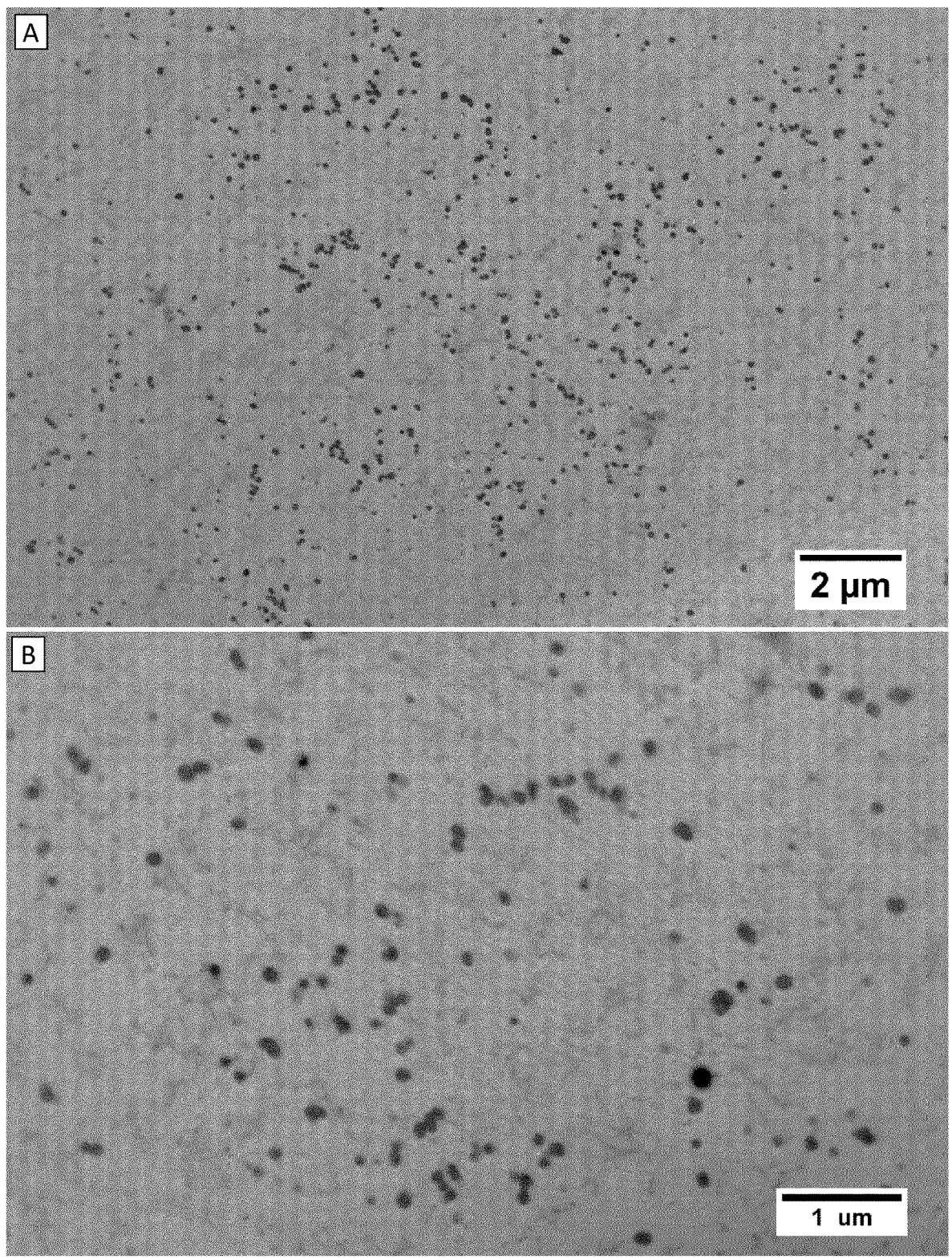

FIG. 2: shows the microgram of the whey micelles dispersion, before the addition of other ingredients according to the inventive process, (A) Scale bar: 2 μm. (B) Scale bar: 1 μm.

Figure 3:
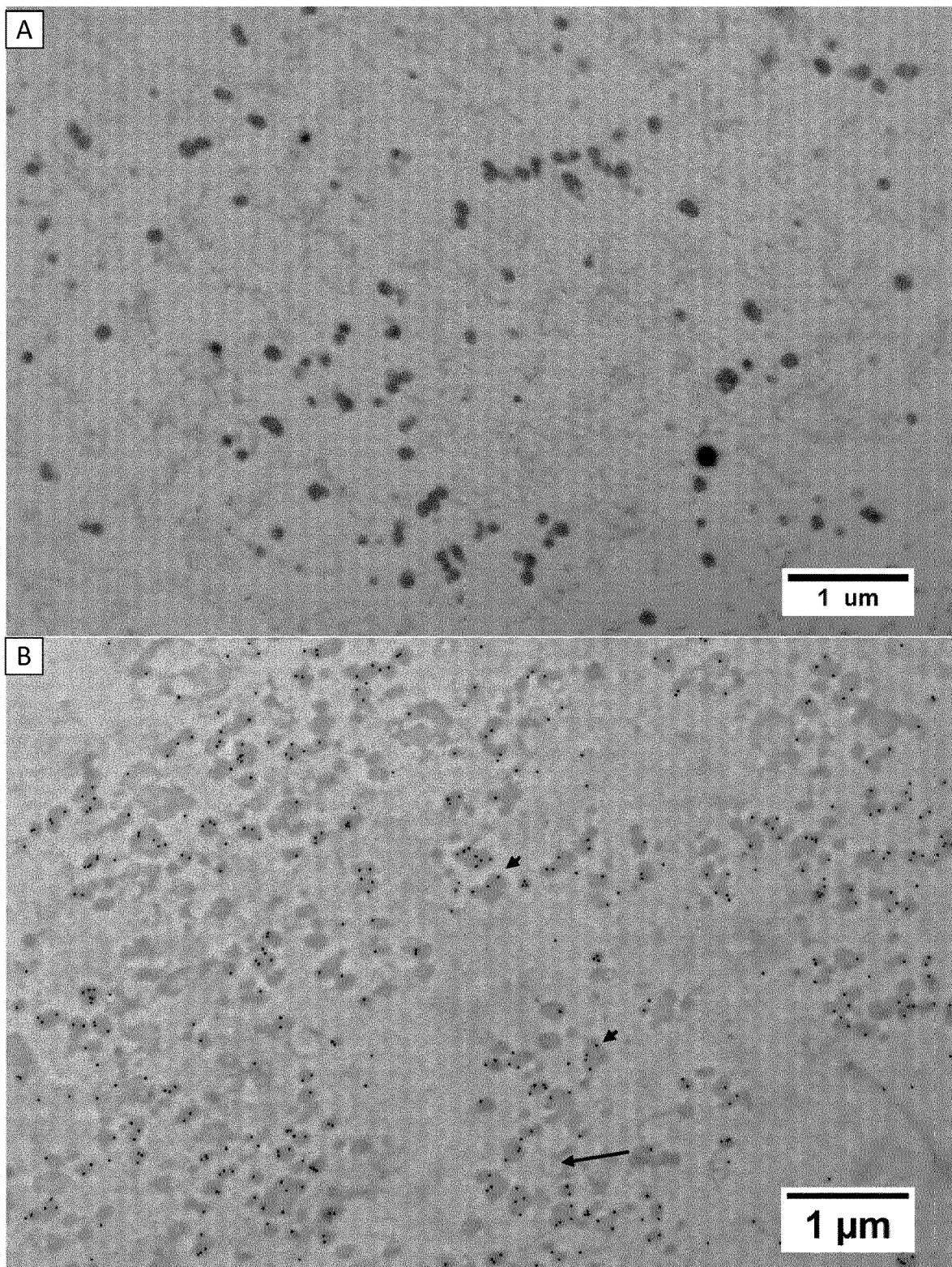
Figure 3:
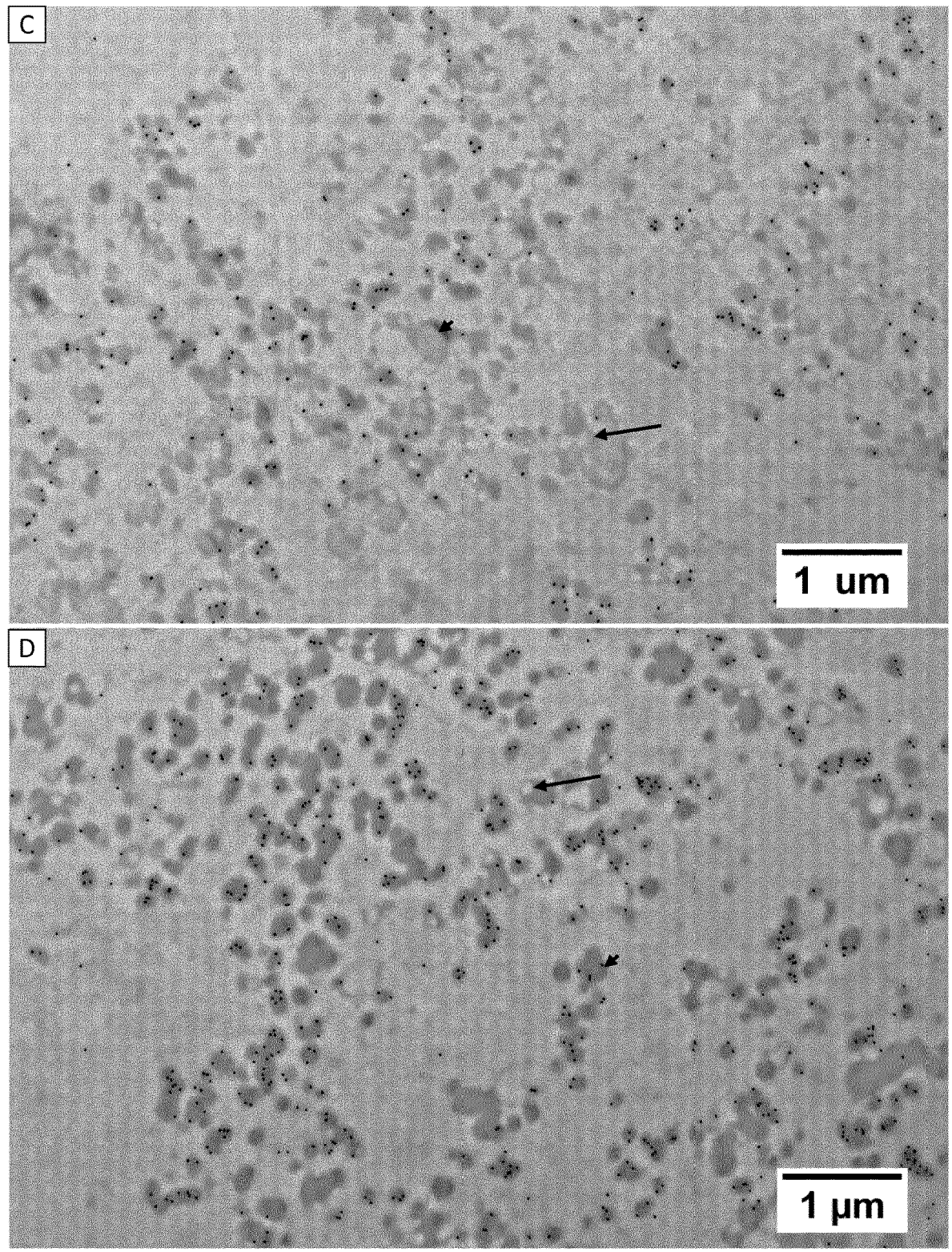

FIG. 3: shows the micrograph of the whey micelles dispersion, before the addition of the other ingredients (A), Example 1 (B), Example 2 (C) and Example 3 (D). In (B), (C) and (D) BLG proteins are localized by immunogold labelling (back dots). Scale bar: 1 μm.

Figure 4:
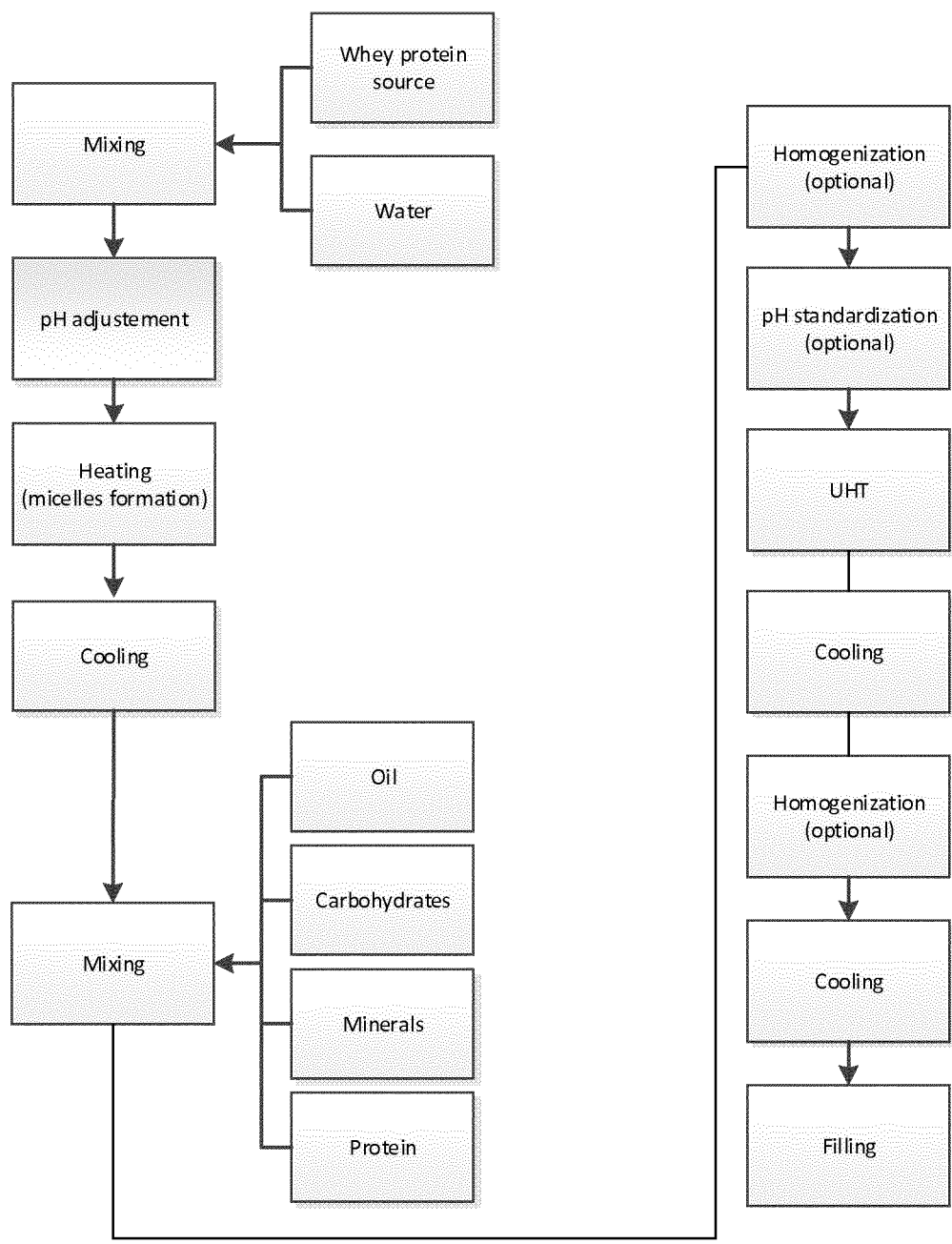

FIG. 4: Schematic for an exemplary inventive process. As one can see the inventive process may (i) provide an aqueous solution comprising whey protein containing whey protein micelles—by heating a whey protein solution. This may then be cooled and optionally fat added followed by mixing. Then (ii) the protein source containing casein is added along with other optional ingredients such as salts and CHO, which may then be (iii) optionally homogenized, then (iv) heat treated, then (v) optionally homogenized.

EXAMPLES

The following examples are intended to illustrate the invention further. They are not intended to limit the subject matter of the invention thereto.

Example 1: Exemplary Process According to the Present Invention

| Ingredient Name | TS [%] | "as is" [kg] | "dry" [kg] |
|---|---|---|---|
| Water (Softened) | — | 68.07 | — |
| Milk protein concentrate, 85% protein content | 95.2 | 10.20 | 9.71 |
| Whey protein isolate | 94.6 | 6.52 | 6.17 |
| Glucose Syrup (DE29) | 95.6 | 7.50 | 7.17 |
| Soybean Oil | 100.0 | 5.00 | 5.00 |
| Sucrose | 99.9 | 2.50 | 2.50 |
| Tripotassium Citrate monohydrate | | 0.15 | 0.14 |
| Sodium Chloride | 99.9 | 0.06 | 0.06 |
| Total | | 100.00 | 30.7 |

The inventive heat sterilized enteral composition according to the present invention containing the above ingredients was prepared as follows using the amounts as defined above. The demineralised water and whey protein isolate were mixed at 50° C. followed by hydration for 30 minutes. A pH adjustment to pH 6.2 was made with citric acid 5% followed by heating the mixture at 85° C. for 15 minutes to form the whey protein micelles, which was then cooled to 15° C.

Soybean oil was then added followed by mixing at 15° C., after which Glucose Syrup (DE29), tripotassium citrate monohydrate, sucrose, sodium chloride and the milk protein concentrate, 85% protein content (casein source) were added with mixing and hydration for 40 minutes.

The mixture was then pre-heated to 50° C. followed by homogenization at 250+50 bar, preheated to 80° C. followed by a UHT treatment by direct steam injection at 148° C. for 5 seconds. This was then flash cooled to 78° C. and the mixture homogenized at 200+50 bar.

Thus, as described above the heat sterilized enteral composition according to the present invention was prepared which contained 14.1% by weight protein, with the following profile:

| | (m)g/100 g | (m)g/100 mL | mg/100 Kcal |
|---|---|---|---|
| Protein g/100 g or mL | 14.1 | 15.3 | |
| Fat g/100 g or mL | 4.9 | 5.3 | |
| Calcium mg/100 g or mL or Kcal | 252 | 274 | 172 |
| Magnesium mg/100 g or mL or Kcal | 14.6 | 16 | 10 |
| Sodium mg/100 g or mL or Kcal | 40 | 43 | 27 |
| Potassium mg/100 g or mL or Kcal | 121 | 132 | 82 |
| Phosphorus mg/100 g or mL or Kcal | 155 | 168 | 106 |
| Chloride mg/100 g or mL or Kcal | 47 | 51 | 32 |
| Citrates mg/100 g or mL or Kcal | 190 | 206 | 129 |
| | | 21.3 | |
| Carbohydrates (difference) | | 12.7 | |
| Kcal/100 mL (calculated) | | 160 | |

Notes:
$Na^+ + K^+$ mg/g protein = 11.4
pH at 25° C. = 6.7
Density @ 20° C. g/cm3 = 1.0868
Total solids = 31.3 g/100 g Furthermore, the amino acids profile was as follows:

| Amino Acid | mg/100 g |
|---|---|
| Tryptophane | 0.250 |
| Methionine, L | 0.373 |
| Cystine, L | 0.242 |
| Aspartic acid | 1.360 |
| Threonine | 0.693 |
| Serine | 0.781 |
| Glutamic acid | 3.000 |
| Proline | 1.190 |
| Glycine | 0.283 |
| Tyrosine | 0.644 |
| Phenylalanine | 0.645 |
| Histidine | 0.348 |
| Lysine | 1.300 |
| Alanine | 0.577 |
| Valine | 0.858 |
| Isoleucine | 0.768 |
| Leucine | 1.570 |
| Arginine | 0.456 |

Notes:
Cystine + Methionine Total [g/100g] = 0.615
Methionine/Cystine (Ratio) = 1.54

Ratio whey/casein calculated based on the equation reported in Ballin, 2006: 48/62

% whey protein=$(C-0.25)/(3.0-0.25) \times 100 = 48\%$

C=percentage of cystine on 100% protein=1.58%

Said heat sterilized liquid enteral composition was without any taste/bitterness. Furthermore this had a viscosity of 44 mPa·s at 20° C./100 s$^{-1}$ as determined using a rheometer (Haake Rheostress 6000 coupled with UMTC) equipped with a plate/plate geometry (60 mm diameter) and 1 mm gap. Flow curves 0-300 s$^{-1}$ (linear increase) were obtained at controlled shear rate at 20° C.+/−0.1.

Furthermore, the obtained liquid enteral composition was shelf stable for 1 year.

Example 2: Exemplary Process According to the Present Invention

| Ingredient name | TS [%] | "as is" [kg] | "dry" [kg] |
|---|---|---|---|
| Water (Softened) | — | 55.03 | — |
| Milk protein concentrate, 85% protein content | 95.2 | 9.00 | 8.57 |
| Whey protein isolate | 94.6 | 6.52 | 6.17 |
| Glucose Syrup (DE29) | 95.6 | 12.70 | 12.14 |
| Soybean Oil | 100.0 | 8.40 | 8.40 |
| Sucrose | 99.9 | 8.20 | 8.19 |
| Tripotassium Citrate | | 0.15 | 0.14 |
| Total | | 100.00 | 43.6 |

The inventive heat sterilized enteral composition according to the present invention containing the above ingredients was prepared as follows using the amounts as defined above. The demineralised water and whey protein isolate were mixed at 50° C. followed by hydration for 30 minutes. A pH adjustment to pH 6.2 was made with citric acid 5% followed by heating the mixture at 85° C. for 15 minutes to form the whey protein micelles, which was then cooled to 15° C.

Soybean oil was then added followed by mixing at 15° C., after which Glucose Syrup (DE29), tripotassium citrate monohydrate, sucrose and the milk protein concentrate, 85% protein content (casein source) were added with mixing and hydration for 40 minutes.

The mixture was then preheated to 80° C. followed by a UHT treatment by direct steam injection at 148° C. for 5 seconds. This was then flash cooled to 78° C. and the mixture homogenized at 200+50 bar.

Thus, a heat sterilized enteral composition according to the present invention was prepared which contained 14.2% by weight protein with the following profile:

| | (m)g/100 g | (m)g/100 mL | mg/100 Kcal |
|---|---|---|---|
| Protein g/100 g or mL | 14.2 | 15.9 | |
| Fat g/100g or mL | 7.3 | 8.2 | |
| Calcium mg/100 g or mL | 252 | 282 | 127 |
| Magnesium mg/100 g or mL | 14.4 | 16 | 7 |
| Sodium mg/100 g or mL | 20 | 22 | 10 |
| Potassium mg/100 g or mL | 115 | 129 | 57 |
| Phosphorus mg/100 g or mL | 155 | 173 | 78 |
| Chloride mg/100 g or mL | 17 | 19 | 9 |
| Citrate mg/100 g or mL | 190 | 212 | 95 |
| Carbohydrates (difference) | | 24.7 21.7 | |
| Kcal/100 mL (calculated) | | 224 | |

Notes:
Na+ + K+ mg/g protein = 9.5
pH at 25° C. = 6.8
Density @ 20° C. g/cm3 = 1.1184
Total solid = 41.5 g/100 g Furthermore, the amino acids profile was as follows:

| Amino Acid | [g/100 g] |
|---|---|
| Tryptophane | 0.242 |
| Methionine, L | 0.374 |
| Cystine, L | 0.240 |
| Aspartic acid | 1.370 |
| Threonine | 0.701 |
| Serine | 0.790 |
| Glutamic acid | 3.050 |
| Proline | 1.220 |
| Glycine | 0.291 |
| Tyrosine | 0.642 |
| Phenylalanine | 0.653 |
| Histidine | 0.360 |
| Lysine | 1.320 |
| Alanine | 0.592 |
| Valine | 0.875 |
| Isoleucine | 0.779 |
| Leucine | 1.600 |
| Arginine | 0.459 |

Cystine + Methionine Total [g/100g] = 0.614
Methionine/Cystine (Ratio) = 1.56.

Ratio whey/casein calculated based on the equation reported in Ballin, 2006: 47/53

% whey protein=$(C-0.25)/(3.0-0.25) \times 100 = 47\%$

C=percentage of cystine on 100% protein=1.54%

Said heat sterilized liquid enteral composition was without any taste/bitterness. Furthermore this had a viscosity of 116 mPa·s at 20° C./100 s$^{-1}$ as determined using a rheometer (Haake Rheostress 6000 coupled with UMTC) equipped with a plate/plate geometry (60 mm diameter) and 1 mm gap. Flow curves 0-300 s$^{-1}$ (linear increase) were obtained at controlled shear rate at 20° C.+/−0.1.

Furthermore, the obtained liquid enteral composition was shelf stable for 1 year.

Example 3: Exemplary Process According to the Present Invention

| Ingredient name | TS [%] | "as is" [kg] | "dry" [kg] |
|---|---|---|---|
| Water (Softened) | — | 57.53 | — |
| Milk Protein concentrate, 85% protein content | 95.2 | 10.20 | 9.71 |
| Whey protein isolate | 94.6 | 6.52 | 6.17 |
| Glucose Syrup (DE29) | 95.6 | 10.80 | 10.32 |
| Soybean Oil | 100.0 | 7.90 | 7.90 |
| Sucrose | 99.9 | 6.90 | 6.89 |
| Tripotassium Citrate | | 0.15 | 0.14 |
| Total | | 100.00 | 41.1 |

The inventive heat sterilized enteral composition according to the present invention containing the above ingredients was prepared as follows using the amounts as defined above. The demineralised water and whey protein isolate were mixed at 50° C. followed by hydration for 30 minutes. A pH adjustment to pH 6.2 was made with citric acid 5% followed by heating the mixture at 85° C. for 15 minutes to form the whey protein micelles, which was then cooled to 15° C.

Soybean oil (was then added followed by mixing at 15° C., after which Glucose Syrup (DE29), tripotassium citrate monohydrate, sucrose and the milk protein concentrate, 85% protein content (casein source) were added with mixing and hydration for 40 minutes.

The mixture was then pre-heated to 50° C. followed by homogenization at 250+50 bar, preheated to 80° C. followed by a UHT treatment by direct steam injection at 148° C. for 5 seconds. This was then flash cooled to 78° C. and the mixture homogenized at 200+50 bar.

Thus, as described above the heat sterilized enteral composition according to the present invention was prepared which contained 12.9% by weight protein, with the following profile:

|  | (m)g/100 g | (m)g/100 mL | mg/100 Kcal |
|---|---|---|---|
| Protein g/100 g or mL | 12.9 | 14.6 |  |
| Fat g/100 g or mL | 7.7 | 8.7 |  |
| Calcium mg/100 g or mL | 223 | 251 | 106 |
| Magnesium mg/100 g or mL | 13.1 | 15 | 6 |
| Sodium mg/100 g or mL | 19 | 21 | 9 |
| Potassium mg/100 g or mL | 118 | 133 | 56 |
| Phosphorus mg/100 g or mL | 136 | 153 | 65 |
| Chloride mg/100 g or mL | 17 | 19 | 8 |
| Citrate mg/100 g or mL | 180 | 203 | 85 |
|  |  | 23.9 |  |
| Carbohydrates (difference) |  | 25.3 |  |
| Kcal/100 mL (calculated) |  | 238 |  |

Notes:
Na$^+$ + K$^+$ mg/g protein = 10.6
pH at 25° C. = 6.7
Density @ 20° C. g/cm3 = 1.1268
Total solid = 43.6 g/100 g Furthermore, the amino acids profile was as follows:

| Amino Acid | [g/100 g] |
|---|---|
| Tryptophane | 0.231 |
| Methionine, L | 0.346 |
| Cystine, L | 0.227 |
| Aspartic acid | 1.240 |
| Threonine | 0.629 |
| Serine | 0.694 |
| Glutamic acid | 2.710 |
| Proline | 1.060 |
| Glycine | 0.256 |
| Tyrosine | 0.557 |
| Phenylalanine | 0.578 |
| Histidine | 0.315 |
| Lysine | 1.160 |
| Alanine | 0.531 |
| Valine | 0.774 |
| Isoleucine | 0.695 |
| Leucine | 1.430 |
| Arginine | 0.402 |

Cystine + Methionine Total [g/100 g] = 0.573
Methionine/Cystine (Ratio) = 1.52.

Ratio whey/casein calculated based on the equation reported in Ballin, 2006: 51/49

% whey protein=$(C-0.25)/(3.0-0.25) \times 100 = 51\%$

C=percentage of cystine on 100% protein=1.64%

Said heat sterilized liquid enteral composition was without any taste/bitterness. Furthermore this had a viscosity of 125 mPa·s at 20° C./100 s$^{-1}$ as determined using a rheometer (Haake Rheostress 6000 coupled with UMTC) equipped with a plate/plate geometry (60 mm diameter) and 1 mm gap. Flow curves 0-300 s$^{-1}$ (linear increase) were obtained at controlled shear rate at 20° C.+/−0.1.

Furthermore, the obtained liquid enteral composition was shelf stable for 1 year.

Example 4: Transmission Electron Microscopy

Protocol:

Samples prepared according to examples 1, 2 and 3 above (termed also "recipes 1, 2 and 3") are fixed in 3.7% paraformaldehyde in PBS buffer (pH: 7.3) after their reception. Fixed samples are embedded in 4% aqueous agar solution and solidified on ice. Small cubes of 1 mm$^3$ are cut and then the samples are dehydrated in graded series of ethanol solution, from 30% to 100%, 30 minutes each bath, and 3 times 1 hour for the 100% ethanol solution. Samples are then gradually infiltrated in graded LR White resin series prior to final infil-tration in pure resin 3 times for 1 hour each. The polymerization is carried out at 60° C. for 48 hours. After polymerization, ultrathin sections of 70 nm are sliced and collected on 100 mesh nickel grids.

For BLG-immunolabelling, grids are placed on drops of 2.5% BSA (w/v) solution in Tris pH 7.4 for 15 min. Grids are then transferred onto drops of Tris containing 1/200 anti-BLG for 1 night at 4° C. They are rinsed 3 times with Tris before incubation on drops of Protein A gold 15 nm diluted 1/30 for 30 min. Then, grids are rinsed with 3 times with Tris before 3 final rinsing steps with water.

Samples are imaged with a Tecnai Spirit BioTWIN using a LaB6 filament at 80 kV electron microscope (FEI, Netherlands).

The results are shown in FIG. 3. FIG. 3 shows the micrograph of the whey micelles dispersion, before the addition of the other ingredients (A), and the final heat sterilized enteral composition according to Example 1 (B), Example 2 (C) and Example 3 (D) herein before.

In all 3 samples (FIG. 3 B, C and D), many protein aggregates (arrowheads) were observed. They are usually in close contact with fat globules, which are, in general, very small. Proteins aggregates are only partially spherical and are in particular, but not only, deformed when stabilizing fat globules (FIG. 3 b, C and D, arrows). The presence of BLG is shown by immunogold labelling in the aggregates. It does not reveal the presence of BLG outside the aggregates. These data clearly evidence that whey protein micelles were contained in the final heat sterilized enteral compositions and were detectable.

The invention claimed is:

1. A liquid heat sterilized enteral composition comprising:
a protein source in an amount of 12 to 20% by weight of the enteral composition, the protein source consisting of whey protein containing whey protein micelles, and a source of casein;
wherein the weight ratio of the casein to the whey protein is in the range of 35:65 to 65:35; and
wherein the enteral composition contains cysteine in an amount of 1.2 to 2.4% by weight of the protein source.

2. The enteral composition according to claim 1, wherein the whey protein is present in an amount of 4.5 to 9% by weight of the enteral composition.

3. The enteral composition according to claim 1, wherein the casein is present in an amount of 3.5 to 13% by weight of the enteral composition.

4. The enteral composition according to claim 1, wherein the enteral composition is a liquid composition having a viscosity below 200 mPa·s at 20° C. measured at a shear rate of 100 s$^{-1}$.

5. The enteral composition according to claim 1, having a protein concentration of up to 20 g/100 g of the enteral composition.

6. The enteral composition according to claim 1, which is in a form selected from the group consisting of a nutritional composition, a nutritional supplement, an infant formula, a follow-up formula, a baby food formula, an infant cereal formula or a growing-up milk, an infant or child's food supplement, a children formula, an adult nutritional composition, a maternal nutritional supplement, a bariatric formula, an elderly nutritional composition and a health care formula.

7. A liquid enteral composition comprising 12 to 20 weight % total protein based on the weight of the liquid enteral composition, the total protein consisting of whey protein containing whey protein micelles, and a source of casein for controlling the viscosity of the liquid enteral composition,
   wherein the weight ratio of the casein to the whey protein is in the range of 35:65 to 65:35, and
   wherein the liquid enteral composition has a pH of 6 to 8, and the liquid enteral composition contains cysteine in an amount of 1.2 to 2.4% by weight of the total protein.

8. A process for preparing a liquid heat sterilized enteral composition comprising total protein in an amount of 12 to 20% by weight of the liquid enteral composition, the total protein comprising casein and whey protein containing whey protein micelles,
   wherein the weight ratio of the casein to the whey protein is in the range of 35:65 to 65:35,
   the process comprising:
   (i) providing an aqueous solution of a protein source comprising whey protein containing whey protein micelles;
   (ii) adding a protein source containing casein; and
   (iii) performing a ultra-high temperature (UHT) heat treatment step above 140° C.

9. The process according to claim 8, wherein the whey protein is present in an amount of 4.5 to 9% by weight of the enteral composition.

10. The process according to claim 8, wherein the casein is present in an amount of 3.5 to 13% by weight of the enteral composition.

11. The process according to claim 8, wherein the liquid heat sterilized enteral composition has a viscosity below 200 mPa·s at 20° C. measured at a shear rate of 100 s$^{-1}$.

12. The process according to claim 8, further comprising drying to form a powder.

13. The process according to claim 8, wherein the total protein consists of casein and whey protein containing whey protein micelles.

14. The process according to claim 8, wherein the liquid enteral composition contains cysteine in an amount of 1.2 to 2.4% by weight of the total protein.

15. The process according to claim 8, wherein the UHT heat treatment is performed at 141-160° C.

16. The enteral composition according to claim 1, wherein the enteral composition contains cysteine in an amount of 1.8 to 2.2% by weight of the protein source.

17. The enteral composition according to claim 1, wherein the weight ratio of casein to whey protein is in the range of 45:55 to 55:45.

18. The enteral composition according to claim 1, wherein the whey protein micelles is present in an amount of 2.5 to 3.5% by weight of the enteral composition.

19. The enteral composition according to claim 7, wherein the liquid enteral composition has a pH of 6.7 to 6.9.

* * * * *